United States Patent [19]

Feltrin

[11] Patent Number: 4,909,040

[45] Date of Patent: Mar. 20, 1990

[54] AUTOMATIC REFRIGERATION APPARATUS PROVIDED WITH A STERILIZED STORAGE COMPARTMENT

[75] Inventor: Flavio Feltrin, Pordenone, Italy

[73] Assignee: Industrie Zanussi S.p.A., Pordenone, Italy

[21] Appl. No.: 234,941

[22] Filed: Aug. 22, 1988

[30] Foreign Application Priority Data

Oct. 14, 1987 [IT] Italy .................................. 34056[U]

[51] Int. Cl.$^4$ ............................................. F25F 3/16
[52] U.S. Cl. .......................................... 62/78; 62/234
[58] Field of Search ........................... 62/155, 234, 78

[56] References Cited

U.S. PATENT DOCUMENTS

| 2,169,081 | 8/1939 | James | 62/78 X |
| 2,257,801 | 10/1941 | Hull | 62/78 X |
| 3,899,896 | 8/1975 | Bryant | 62/155 |

FOREIGN PATENT DOCUMENTS 2703949  8/1978  Fed. Rep. of Germany .......... 62/78

Primary Examiner—Harry B. Tanner
Attorney, Agent, or Firm—Wenderoth, Lind & Ponack

[57] ABSTRACT

An automatic refrigerator includes a sterilized storage compartment, normally kept at a food storage temperature, in which a blower provides forced ventilation. A germicide lamp, capable of generating ultraviolet radiations, is located in the flow path of the forced ventilation and is associated with a shielding device protecting the storage compartment from the radiations.

4 Claims, 1 Drawing Sheet 4,909,040

AUTOMATIC REFRIGERATION APPARATUS PROVIDED WITH A STERILIZED STORAGE COMPARTMENT

BACKGROUND OF THE INVENTION

The present invention relates to an automatic refrigeration apparatus, in particular of a domestic type, including a storage compartment intended for keeping foodstuffs or other items at a required temperature, e.g. within a range of between approximately 0° C. and 10° C.

It is common knowledge that these particular storage conditions normally favor the development within the storage compartment of certain mods, yeasts and bacterial spores which affect the good preservability of such food or other items, and which should therefore most desirably be eliminated.

As is known, a most efficient way to eliminate molds, yeasts and bacterial spores consists in subjecting these micro-organisms to the action of ultraviolet radiation, as may be generated for example by UV lamps currently available on the market. On the other hand, the use of such UV lamps for irradiating the inner space of a refrigerating apparatus is not immediately feasible, as it is known that ultraviolet radiation produces in the long run devastating effects on both the appearance and the structure of the materials, mainly plastics, of which most components of the storage compartment of the refrigerator are made.

SUMMARY OF THE INVENTION

It is the object of the present invention to provide a refrigeration apparatus which is equipped with such simple means as to ensure an effective sterilization of the storage compartment, while excluding all undesired impairing side effects on the materials of the components of the compartment.

Such an object is achieved by an automatic refrigeration apparatus including a sterilized storage compartment which is normally kept at a food storage temperature, as well as blowing means capable of providing forced ventilation inside the storage compartment. According to the invention, the refrigeration apparatus further includes germicide means, capable of generating ultraviolet radiation, which are located in the flow path of the forced ventilation and are associated with shielding means protecting the storage compartment from the radiation.

In a preferable arrangement, the germicide means and the blowing means are operated simultaneously during at least a portion of the defrosting cycles of the refrigeration apparatus.

BRIEF DESCRIPTION OF THE DRAWINGS

The invention will be further described by way of a non-limiting example with reference to the accompanying drawings, in which.

DETAILED DESCRIPTION OF THE INVENTION

Figure 1:
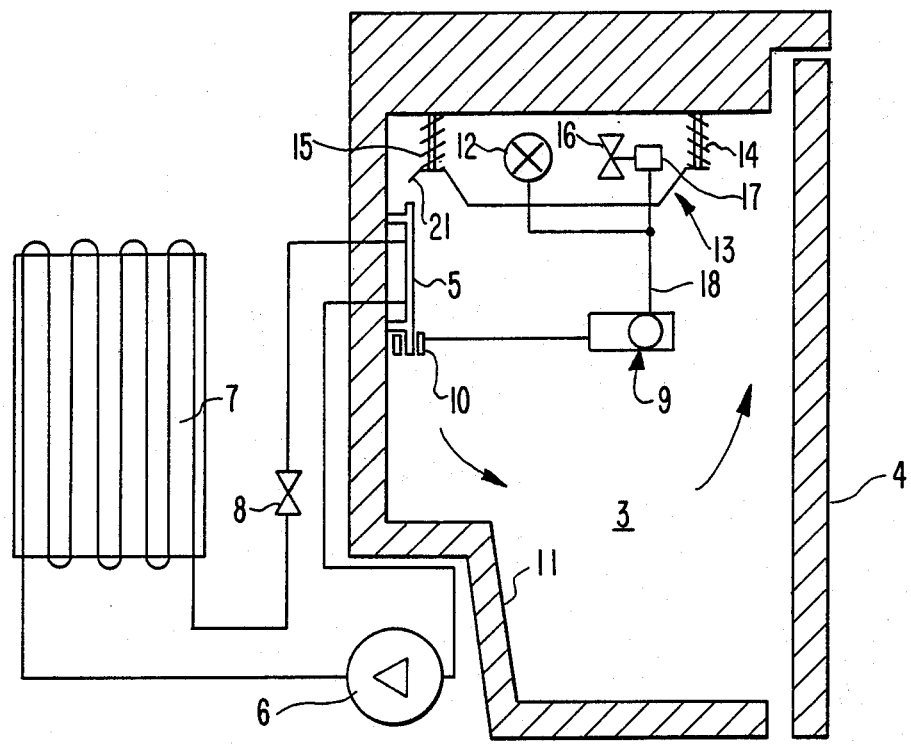
FIG. 1 is a basic schematic view of a preferred embodiment of the invention.

Referring in particular to FIG. 1, the refrigeration apparatus according to this invention mainly includes a storage compartment 3, which is normally defined by a plastic liner 11, and to which access is gained through a door 4. The storage compartment is cooled by an evaporator 5 which is part of a conventional-type refrigerating circuit, such as for example a circuit including also a compressor 6, a condenser 7 and a throttling device 8.

In a per se known manner, a thermostatic temperature control device 9 is actuated by at least one probe 10 which is intended to detect the temperature of the evaporator 5 so as to most suitably initiate and terminate the operation of cycles of the compressor 6.

The control device 9 of course also can be actuated by a probe (not shown for the sake of simplicity) intended for detecting the temperature prevailing inside the storage compartment 3. In all cases, however, the refrigerating circuit will be controlled so as to maintain the storage compartment 3 within a selected refrigeration temperature range, e.g. normally ranging from approximately 0° C. to 10° C. As is known, such temperature conditions, when combined with normally prevailing humidity conditions, can give rise to the development of molds, yeasts and bacterial spores inside the storage compartment 3. To eliminate these micro-organisms, the refrigerator is provided with germicide means 12, which are preferably located in a place inside the storage compartment 3 and are capable of generating ultraviolet radiations. In particular, germicide means 12 can consist of at least one UV lamp capable of generating C-type ultraviolet radiations, i.e. radiations having a wavelength equal to 2537 A. For example, a lamp that could be used for this application is the TUV 6W lamp marketed by Philips. However, as already mentioned, this is contrary to a technical prejudice, since ultraviolet radiations can alter the appearance and the structure of the walls and other components of the storage compartment 3, which are made of plastics.

According to a feature of this invention, such particular disadvantage is substantially eliminated by having the lamp 12 suitably associated with appropriate shielding means 13, which are capable of preventing the walls of the storage compartment 3 from being exposed to ultraviolet radiations. In a preferred embodiment, shielding means 13 include a housing designed to accommodate the UV lamp and preferably made of reflecting metal, such as aluminum. The housing 13 is provided with inlet openings 14 and outlet openings 15 for an air flow which is circulated inside the storage compartment 3 by a motor-driven fan 16 or the like which is also located inside the housing 13. Openings 14 and 15 are sized and shaped in an appropriate manner so as to keep leakage of ultraviolet radiations from the housing 13 to a minimum.

The accommodation of the fan 16 in the storage compartment 3 is per se known, for example as disclosed in Italian Patent Application No. 45733 A/87, filed on Jul. 9, 1987. According to a feature of this invention, the motor 17 of the fan 16 and the lamp 12 are arranged so as to be operated at the same time by a control output 18 of the thermostatic device 9, this being preferably made to occur during the automatic defrosting periods of the evaporator 5 which are determined in a per se known way by the refrigerating circuit 5-10.

Figure 2:
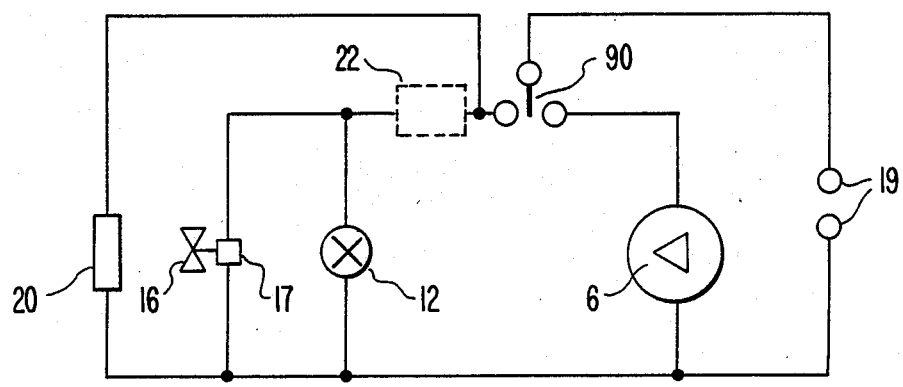
FIG. 2 is a wiring diagram showing a control system for a refrigerator according to the embodiment of FIG. 1.

To this end, as is shown in FIG. 2, the thermostatic device 9 includes a changeover switch 90 having two switching positions based on the temperature detected by the probe 10, in which positions it is arranged to connect to the terminals 19 of the power supply source either the compressor 6 or the parallel-connection of the lamp 12 and the motor 17 of the fan 16. In a preferred embodiment, a heater 20 for defrosting the evaporator 5 would also be connected in parallel to the lamp 12 and the motor 17.

The operation of the refrigerator according to this invention is apparent. When a relatively high temperature is detected by the probe 10, the thermostatic device 9, 90 will switch on the compressor 6, whereas both the lamp 12 and the fan 16 will be switched off. When a relatively low temperature is detected by the probe 10, the compressor 6 will be switched off by the thermostatic device 9, 90 which will on the other hand switch on both the lamp 12 and the motor 17 of the fan 16, as well as, if provided, the defrost heater 20. Under these conditions, the refrigerator goes therefore through a defrosting operation of the evaporator 5, during which the fan 16 circulates inside the storage compartment 3 a forced-air flow that, being conveyed to pass through the housing 13 of the lamp 12, is sterilized by the UV lamp 12 and, as a consequence, will itself sterilize the storage compartment 3 where it is circulated.

It has experimentally been found that such periodically occurring action of ultraviolet radiation causes molds, yeasts and bacterial spores inside the storage compartment 3 to be effectively eliminated, while the components forming the storage compartment 3 themselves are not exposed to the radiations at all. It should further be noted that the operation of the fan 16 only during the defrost periods prevents the storage compartment environment from undesirably drying up in a too severe manner. Quite the contrary, the forced air circulation during the defrost cycles of the evaporator 5 allows the humidity that was previously condensed and frosted on the evaporator surface to be advantageously recovered into the storage compartment space. In order to enhance its effectiveness in this sense, the air flow circulated by the fan 16 can be suitably directed towards the evaporator 5 by means of a baffle 21 or similar arrangement.

It will be appreciated that the above described refrigeration apparatus may be the subject of any modifications considered to be appropriate, without departing from the scope of the invention.

For example, in order to limit the periods of operation of the UV lamp 12 and the fan 16, these could advantageously be only switched on during a portion of each defrost period. This could for example be implemented by connecting the lamp 12 and the motor 17 to the changeover switch 90 through a timing device 22 (shown by dashed line in FIG. 2). Device 22 may be made to include a timer switch of a per se known type, which could for example be controlled by an RC-device having a time constant which is shorter than the average duration of a defrost cycle of the refrigerator.

I claim:

1. An automatic refrigeration apparatus comprising:
   a sterilizing storage compartment which is normally kept at a food storage temperature, said compartment comprising material damageable by ultraviolet radiations and exposed at the interior of the compartment;
   blowing means capable of providing forced ventilation inside said storage compartment;
   germicide means for generating ultraviolet radiations disposed in said compartment in the flow path of said forced ventilation; and
   shield means disposed in said compartment over said germicide means for preventing the material forming said storage compartment from being exposed to said radiations, said shielding means consisting of material which is not damageable by the ultraviolet radiations.

2. An apparatus according to claim 1, further comprising a refrigeration circuit capable of automatically performing cyclical evaporator defrost operations and including control means for operating said germicide means and said blowing means at the same time during at least a portion of periods of said defrost operations.

3. An apparatus according to claim 1, wherein said shielding means is a housing mounted to said compartment, said housing having means defining inlet and outlet openings extending through the housing and substantially preventing ultraviolet radiations generated by said germicide means from irradiating said material, said flow path extending through said inlet and said outlet openings.

4. An apparatus according claim 3, wherein said housing means is disposed over said blowing means.

* * * * *